United States Patent [19]

Schubert et al.

[11] 4,176,661

[45] Dec. 4, 1979

[54] PHOTOENDOSCOPE HAVING A DISTAL ELECTRONIC FLASH-TUBE GUARD

[75] Inventors: Herbert Schubert; Siegfried Hiltebrandt, both of Knittlingen, Fed. Rep. of Germany

[73] Assignee: Richard Wolf GmbH, Knittlingen, Fed. Rep. of Germany

[21] Appl. No.: 834,864

[22] Filed: Sep. 20, 1977

[30] Foreign Application Priority Data

Sep. 25, 1976 [DE] Fed. Rep. of Germany ....... 2643233

[51] Int. Cl.² ............................................. A61B 1/04
[52] U.S. Cl. .............................................. 128/6; 354/62; 362/10; 362/376
[58] Field of Search ........................................ 128/4–9, 128/303.15; 362/10, 376, 377; 354/62

[56] References Cited

U.S. PATENT DOCUMENTS

| 879,224 | 2/1908 | Wappler | 128/7 |
|---|---|---|---|
| 1,199,731 | 9/1916 | Ilgner | 128/6 |
| 2,228,680 | 1/1941 | Tornblom | 362/376 |
| 2,541,976 | 2/1951 | Bogart | 128/6 X |
| 2,789,205 | 4/1957 | Schwartz et al. | 362/10 |
| 3,253,524 | 5/1966 | Ashizawa et al. | 128/4 X |
| 3,256,875 | 6/1966 | Tsepeleu et al. | 128/8 |
| 3,297,022 | 1/1967 | Wallace | 128/6 |
| 3,593,706 | 7/1971 | Schubert | 128/8 |
| 3,808,495 | 4/1974 | Win | 362/376 X |
| 4,042,819 | 8/1977 | Dacal | 362/376 X |

FOREIGN PATENT DOCUMENTS 435358 2/1912 France ........................................ 128/8

Primary Examiner—Clifford D. Crowder
Assistant Examiner—Steven A. Bratlie
Attorney, Agent, or Firm—Kinzer, Plyer, Dorn & McEachran

[57] ABSTRACT

A photoendoscope comprising a telescope tube defining, near its distal end a viewing port, flash-tube assembly means connected to the distal end of the telescope tube and including a flash-tube proper enveloped in transparent protective sheath means arranged in a housing defining an aperture for transmitting light from the flash-tube proper and light conductor means extending along the telescope tube and terminating proximally of said viewing port, a barrel enclosing said telescope tube and said light conductor means at least in their distal end regions, and said flash-tube means, said barrel defining two apertures aligning respectively with said viewing port and with said flash-tube light transmitting aperture, and a transparent cylindrical sheath which is secured in said barrel, which extends for approximately the length of said flashtube proper and which covers said flash-tube light transmitting aperture, said transparent cylindrical sheath having a wall thickness which is greater where it covers said flash-tube light transmitting aperture than in the remainder of the sheath.

4 Claims, 4 Drawing Figures

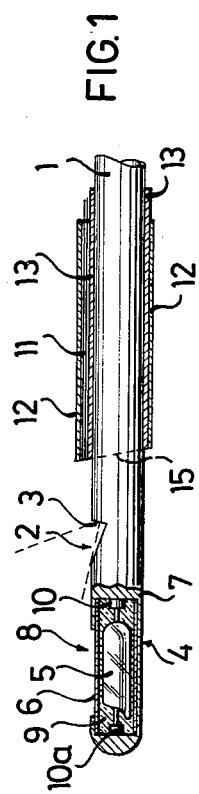
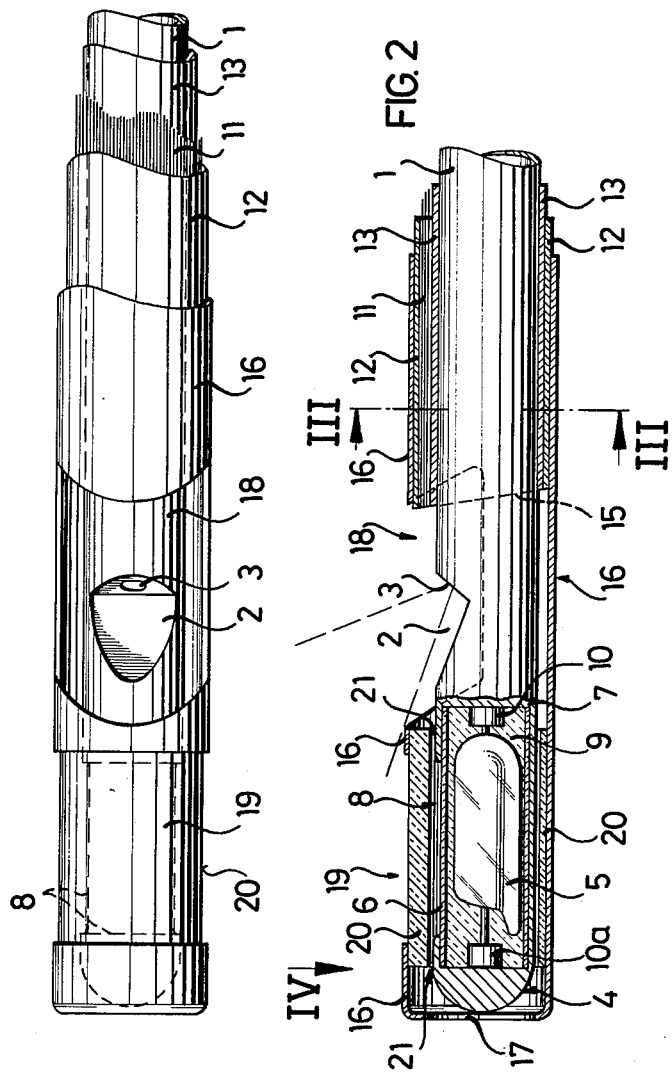
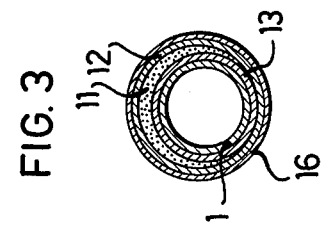

PHOTOENDOSCOPE HAVING A DISTAL ELECTRONIC FLASH-TUBE GUARD

BACKGROUND OF THE INVENTION

1. Field of the Invention

The invention relates to photo-endoscope having an electronic flash-tube and more particularly to a photo-endoscopes having an electronic flash-tube inserted in a metal telescope tube on the distal side of the viewing port, the flash-tube being provided with an enveloping transparent protective sheath and together with a transparent cast substance being arranged in a metal housing provided with an aperture lying in the viewing direction, a fibre light-conductor of crescent-shaped cross-section being positioned around the telescope tube between two mutually eccentric tubes and terminating with its maximum thickness on the proximal side of the viewing port of the telescope. Such a photoendoscope may be referred to as an endoscope of the kind described.

2. Description of the Prior Art

It is known to arrange an electronic flash-tube at the proximal end of a photoendoscope and to conduct not only the normal light for observation but also an electronic flash to produce photos into a body cavity by means of a light-conducting cable. This proximal photographic illumination by means of the flash-tube presents no danger to the doctor or patient but does involve considerable expense.

When endoscope telescopes of large diameter can be used, it has been the practice because of the lower cost, to mount the electronic flash-tube in the distal end of the telescope, which gives a picture of better quality and, because of the wide angle of illumination, optimum lighting of the object and the surroundings. A disadvantage however is the risk of the electronic flash-tube fracturing as a result of the fact that, although the tubes are of small dimensions, large amounts of electrical energy are released when the flash is triggered. With aim of preventing splinters from penetrating the body cavity should the flash-tube explode or burst, flash tubes arranged in a holder formed by a housing have already been enclosed in transparent protective sleeves and the space between the flash tube and the protective sleeve filled with a transparent, usually cast, heat-resistant substances. This however does not provide complete protection since under certain circumstances the protective sheath itself may burst or splits may develop in the sheath with the result that splinters from the flash-tube or the transparent cast substance enclosing the flash-tube can find their way into the body cavity, which may be harmful to the patient and create considerable problems for the doctor.

The main object of the invention is therefore to provide satisfactory protection against splinters or the like penetrating into the body cavity in the event of the electronic flash-tube bursting, as it may under certain circumstances.

SUMMARY OF THE INVENTION

In a photoendoscope of the kind described at the beginning, this is achieved in accordance with the invention by surrounding the electronic flash-tube and the light conductor with a metal barrel which has cut-outs for the viewing port and for the light from the flash tube, and by securing in the distal end of the barrel a transparent cylindrical sheath which extends for approximately the length of the flash-tube and whose wall thickness is increased in the area where the light from the flash-tube emerges.

By this means protection against splinters is provided not only by a known protective sheath but also by a transparent cylindrical sheath whose wall thickness is increased in the area where the light from the flash tube emerges and which is secured in the distal end of an additional metal barrel, e.g. is cemented in place, so that in this way splinters or the cast substance can be in all cases be prevented from penetrating into the body cavity even if the known protective sheath should rupture or develop splits if the flash-tube bursts.

BRIEF DESCRIPTION OF THE DRAWINGS

FIG. 1 is a side view, partly in axial section, of the distal end of a known photoendoscope, FIG. 2 is an enlarged-scale side view, partly in axial section, of the distal end of a photoendoscope constructed in accordance with the invention, FIG. 3 is a cross-section on line III—III of FIG. 2, FIG. 4 is a plan view of FIG. 2 looking in the direction of arrow IV.

In the drawings, the same reference characters are used to designate the same or similar parts.

The photoendoscope shown in FIG. 1 consists in a known fashion of an endoscope telescope 1 which has a cut-out 2 back from its distal end and a viewing port 3 for vision obliquely forward into the field illuminated by an electronic flash-tube assembly 4 which can be screwed into the distal end of the telescope. The flash-tube assembly 4 consists of the flash-tube proper 5, a transparent protective sheath 6 made of heat-resistant plastics material or the like, a metal barrel or housing 7 which acts as a holder and which, in the plane of the viewing port 2, 3 is provided with an opening 8 to allow the flash of light to emerge and a hemispherical end cap. The cylindrical protective sheath 6 and the flash-tube 5 are encapsulated in a transparent plastics material 9 cast in the metal holder 7. When the flash tube assembly is screwed into the distal end of the telescope, high frequency (HF) current reaches a terminal 10 of the flash tube proper 5 from an insulated HF lead extending through the telescope 1. An earth terminal 10a of the flash-tube proper is in contact with the metal housing 7 and thus with the metal telescope tube 1.

The telescope 1 is provided proximally with an eyepiece (not shown) and the HF lead can be connected to a cable leading to an HF generator by means of a suitable connection at the side of the telescope.

For normal investigatory observation of a body cavity, a fibre light-conductor 11 is positioned around the telescope 1, this light-conductor terminating at 15 on the proximal side of the viewing port 2 and being so arranged between two mutually eccentric tubes 12 and 13 that it is crescent-shaped in cross-section and its greatest thickness lies on the longitudinally extending central plane of the viewing port 2, 3. Proximally the light-conductor 11 is coupled laterally to a connection to which a light-conducting cable leading to a light-source can be connected.

DESCRIPTION OF THE PREFERRED EMBODIMENT

In accordance with the invention, and as shown in FIGS. 2 to 4, an additional metal barrel or housing 16 is provided which can be slid over the light conductor 11, or rather its outer envelope tube 12, and at the distal end of the telescope 1 this barrel terminates level with or slightly to either side of the hemispherical end cap of the electronic flash-tube assembly 4. All round the distal end of the barrel 16 a portion of it is folded inwards so that an unobstructed aperture 17 is left which is at least equal in size to the diameter of the flash-tube assembly 4 and which allows the tube to be replaced. The barrel 16 is provided with a cut-out aperture 18 for the viewing port 2, 3 and for the light from the light conductor 11 and with a cut-out 19 for the light from the flash tube 5. In the area where the cut-out 19 is situated, a transparent cylindrical sheath 20 made of heat-resistant material whose bore is eccentric is cemented securely into the barrel 16. The cylindrical eccentrically-bored sheath lies with its maximum wall thickness in the longitudinally extending centre plane of the viewing port 2, 3 or of the cut-out 19, in the same way as the fibre light conductor 11 which lies with its maximum thickness in this plane. Proximally there is a known interlock or locating arrangement provided which is not shown for reasons of clarity and which ensures that when the barrel 16 is slid on, the cut-outs 18 and 19 will be situated in the correct position relative to the cut-out 2 in the telescope 1.

Between the cylindrical sheath 20 and the housing 7 of the flash-tube assembly there is a small gap 21 at both ends through which any gases which may be released should the electronic flash-tube explode and the protective sheath 6 be burst can escape to the exterior through cut-out 18 and aperture 17. Under no circumstances will splinters of the flash-tube or the cast plastics material 9 be able to find their way out into the body cavity since this is prevented by the thick walled cylindrical sleeve 20 in the area of cut-out 19.

In the drawings the distal portion only of the photoendoscope has been shown for reasons of clarity and also because the more proximal parts of photoendoscopes are well known by those skilled in the art and do not per se form part of the invention.

We claim:

1. In a photoendoscope comprising a telescope tube defining a viewing port near its distal end, flash-tube assembly means connected to the distal end of the telescope tube and including a flash-tube proper enveloped in transparent protective sheath means, arranged in a housing defining an aperture for transmitting light from the flash-tube proper, and light conductor means extending along the telescope tube and terminating proximally of said viewing port, the improvement comprising:
    (a) a barrel enclosing the flash-tube assembly means and at least the distal end regions of the telescope tube and the light conductor means,
    (b) two apertures formed in the barrel and aligned respectively with the viewing port and with the flash-tube assembly light transmitting aperture,
    (c) a transparent cylindrical sheath which is secured in the barrel and which covers the flash-tube assembly light transmitting aperture, said transparent cylindrical sheath having a wall thickness which is greater where it covers said flash-tube assembly light transmitting aperture than in the remainder of the sheath.

2. A photoendoscope as claimed in claim 1, wherein said transparent protective sheath means comprise a transparent protective sheath and a transparent cast material encapsulating said sheath, and said light conductor means comprises a fibre light-conductor of crescent-shaped cross-section positioned around said telescope tube between two mutually eccentric tubes and terminating with its maximum thickness on a proximal side of said viewing port.

3. A photoendoscope as claimed in claim 1, wherein said transparent cylindrical sheath is of heat-resistant material, and is cemented into the distal end of said barrel, said cylindrical sheath defining at either end annular gaps between the sheath and the periphery of said housing of said flash-tube assembly means, the annular gaps being open towards the said aperture in said barrel which aligns with said viewing port and a concentric aperture in and defined by the distal end of said barrel.

4. A photoendoscope according to claim 1, wherein the distal end of said barrel defines a concentric aperture at least corresponding in cross-section to the said housing of said flash-tube assembly means.

* * * * *